(12) United States Patent
McGuire et al.

(10) Patent No.: US 9,452,007 B1
(45) Date of Patent: Sep. 27, 2016

(54) CANNULATED SCREW SYSTEM

(75) Inventors: David A. McGuire, Anchorage, AK (US); Bruce D. Sunstein, Rockport, MA (US)

(73) Assignee: David A. McGuire, Anchorage, AK (US)

(*) Notice: Subject to any disclaimer, the term of this patent is extended or adjusted under 35 U.S.C. 154(b) by 933 days.

(21) Appl. No.: 13/566,713

(22) Filed: Aug. 3, 2012

Related U.S. Application Data

(60) Provisional application No. 61/514,945, filed on Aug. 4, 2011.

(51) Int. Cl.
*A61B 17/04* (2006.01)
*A61B 17/86* (2006.01)

(52) U.S. Cl.
CPC .................. *A61B 17/8615* (2013.01)

(58) Field of Classification Search
CPC ....................... A61B 17/86–17/8695
USPC ......................... 606/104, 304, 321
See application file for complete search history.

(56) References Cited

U.S. PATENT DOCUMENTS

| | | | |
|---|---|---|---|
| 3,208,318 A | 9/1965 | Roberts | |
| 4,911,593 A * | 3/1990 | Kephart | 411/403 |
| 4,927,421 A | 5/1990 | Goble et al. | 606/73 |
| 5,391,170 A | 2/1995 | McGuire et al. | 606/86 |
| RE34,871 E | 3/1995 | McGuire et al. | 606/73 |
| 5,470,334 A | 11/1995 | Ross et al. | 606/72 |
| 5,520,693 A | 5/1996 | McGuire et al. | 606/86 |
| 5,562,669 A | 10/1996 | McGuire | 606/72 |
| 5,797,918 A | 8/1998 | McGuire et al. | 606/104 |
| 2001/0004694 A1* | 6/2001 | Carchidi et al. | 606/73 |
| 2003/0074003 A1* | 4/2003 | Deslauriers et al. | 606/73 |
| 2006/0004378 A1* | 1/2006 | Raines et al. | 606/99 |
| 2006/0189991 A1* | 8/2006 | Bickley | A61B 17/864 606/916 |
| 2008/0269768 A1* | 10/2008 | Schwager et al. | 606/104 |
| 2009/0306777 A1* | 12/2009 | Widmer | A61B 17/0401 623/13.14 |
| 2010/0152740 A1* | 6/2010 | O'Reilly et al. | 606/87 |
| 2010/0222827 A1* | 9/2010 | Griffiths et al. | 606/309 |
| 2011/0306984 A1* | 12/2011 | Sasing | 606/104 |

OTHER PUBLICATIONS

Bernard R. Bach, Jr., MD., "Observations on Interference Screw Morphologies," Special Report, *Arthroscopy: The Journal of Arthroscopic and Related Surgery*, vol. 16, No. 5, (Jul.-Aug.), 2000:E10, pp. 1-6.

(Continued)

*Primary Examiner* — Matthew Lawson
(74) *Attorney, Agent, or Firm* — Sunstein Kann Murphy & Timbers LLP

(57) ABSTRACT

A cannulated driver includes a handle, a barrel coupled to the handle, and a drive tip coupled to the barrel and having an outer surface and an engagement end that engages within a head of a cannulated screw. The driver is configured to removably retain a corresponding cannulated screw onto the driver. The drive tip includes a passageway disposed generally in a radial direction with respect to the driver's longitudinal axis. An engagement pin is movably mounted for travel in the passageway between an extended position wherein an exposable end of the pin protrudes radially beyond the outer surface of the drive tip and a retracted position wherein the pin does not thus protrude. In the extended position, the exposable end of the pin protrudes into a corresponding recess in the head of a special cannulated screw to removably retain the screw onto the driver.

9 Claims, 3 Drawing Sheets

(56) References Cited

OTHER PUBLICATIONS

Christine Trepanier, et al., "Corrosion Resistance and Biocompatibility of Passivated Nitinol," *Shape Memory Implants,* 2000, 12 pages.

"Nitinol Materials and Components from NDC—Nitinol Facts," *NDC—Nitinol University,* http://www.nitinol.com/nitinol-university/nitinol-facts/ [May 21, 2011 5:48:30 PM], 5 pages.

* cited by examiner ically disposed recess formed in the head of the screw to retain the screw on the drive tip and in the retracted position the pin ceases to retain the drive tip so as to enable it to be removed from the head of the screw.

CANNULATED SCREW SYSTEM

RELATED APPLICATION

The present invention claims the benefit of and priority from U.S. provisional application Ser. No. 61/514,945, filed Aug. 4, 2011, which application is hereby incorporated herein by reference in its entirety.

TECHNICAL FIELD

The present invention relates to cannulated screws and drivers for them, and more particularly to systems of cannulated screws and drivers for surgical applications among others.

BACKGROUND ART

U.S. Pat. No. 4,927,421 discloses a method of reconstruction of a ligament using a cannulated interference screw to secure the reconstructed ligament to a bone tunnel. In various embodiments disclosed therein, the cannulated interference screw is secured in place using a cannulated driver. A cannulated driver is also disclosed in U.S. Pat. No. 5,797,918. The cannulated driver and cannulated interference screw may be oriented in relation to one another by sliding the screw and the driver down a Kirscher wire.

Other embodiments of a driver for a cannulated screw are disclosed in U.S. Pat. No. 5,391,170; this driver is equipped with an arrangement for releasably retaining a cannulated screw for ease of inserting the screw. However, this driver is not cannulated.

It is known in the prior art to provide a socket wrench that can releasably retain a socket, as shown in U.S. Pat. No. 3,208,318. The socket wrench of that patent is not cannulated.

All patents referenced in this section are hereby incorporated herein by reference.

SUMMARY OF THE EMBODIMENTS

In a first embodiment of the invention there is provided a cannulated driver that includes a handle; a barrel coupled to the handle; and a drive tip coupled to the barrel and having an outer surface and an engagement end that engages within a head of a cannulated screw. The handle, barrel, and drive tip are cannulated so as to include a bore along a longitudinal axis.

The driver of this embodiment is equipped to removably retain a corresponding cannulated screw onto the driver. In this embodiment, the drive tip includes a passageway disposed generally in a radial direction with respect to the longitudinal axis. An engagement pin is movably mounted for travel in the passageway between an extended position wherein an exposable end of the pin protrudes radially beyond the outer surface of the drive tip and a retracted position wherein the pin does not thus protrude. In the extended position, the exposable end of the pin protrudes into a corresponding recess in the head of a special cannulated screw to removably retain the screw onto the driver.

The cannulated driver of this embodiment further includes an actuator that causes movement of the engagement pin in at least one direction between the retracted position and the extended position. It also includes a user-operable trigger, mounted near the handle, and coupled to the actuator, configured so that the user can selectively cause the pin to occupy either the extended position or the retracted position.

With this embodiment, in the extended position, the pin can enter a corresponding radially disposed recess formed in the head of the screw to retain the screw on the drive tip and in the retracted position the pin ceases to retain the drive tip so as to enable it to be removed from the head of the screw. When the cannulated screw is retained on the drive tip, the screw and the driver can be slid along a guide wire disposed in the bore of the driver.

In a further related embodiment, the drive tip further includes a pin bias spring to bias the pin in one of the retracted and extended positions and the actuator is configured to move the pin to the other of the extended and retracted positions. Optionally, the pin bias spring is configured to bias the pin in the retracted position and the actuator is configured to move the pin to the extended position. Optionally, the actuator includes a hollow sheath concentrically disposed inside the barrel and axially movable therein between a first position in which it is proximate to the engagement end of the drive tip and a second position in which it is not; and the pin bias spring is a leaf spring mounted inside the barrel with a long dimension disposed axially and having a first end affixed to the barrel and a second end, located closer than the first end to the engagement end of the drive tip and affixed to the pin, the second end disposed to protrude radially inward when the pin is the retracted position. Under this option, the spring is so disposed that when the sheath is in the first position, the sheath urges the second end of the leaf spring and therefore the pin in a radially outward direction so as to move the pin into the extended position, and, when the sheath is in the second position, the second end of the leaf spring is unimpeded by the sheath and therefore the pin occupies the retracted position. As a further option the cannulated driver has a sheath bias spring configured to bias the sheath in the first position. In a further related embodiment, the exposable end of the engagement pin is tapered and, optionally, also rounded.

In a related embodiment, the actuator includes a rack and pinion assembly disposed in the drive tip. Alternatively or in addition, the drive tip is shaped to accommodate the actuator therein. Also alternatively or in addition, the drive tip has a cross section that is radially asymmetrical so as to define a unique orientation within the head of the screw.

A further embodiment of the present invention is similar to the embodiment previously described employing a leaf spring, wherein the actuator and trigger are dispensed with. In this embodiment there is provided, as before, a handle, a barrel coupled to the handle, a drive tip coupled to the barrel and having an outer surface and an engagement end that engages within a head of a cannulated screw, and wherein the handle, barrel, and drive tip are cannulated so as to include a bore along a longitudinal axis. The drive tip similarly, as before, includes a passageway disposed generally in a radial direction with respect to the longitudinal axis, and an engagement pin movably mounted for travel in the passageway between an extended position wherein an exposable end of the pin protrudes radially beyond the outer surface of the drive tip and a retracted position wherein the pin does not thus protrude.

In this embodiment, the engagement pin is configured in relation to the drive tip so that, in the extended position, only a rounded portion of the engagement pin protrudes radially beyond the outer surface of the drive tip. A pin bias spring biases the pin in the extended position, so as to establish a detent mechanism in cooperation with the engagement pin in the drive tip. In this embodiment, first, in the extended position, the pin can enter a corresponding radially disposed recess formed in the head of the screw to retain the screw on the drive tip and in the retracted position the pin ceases to retain the drive tip so as to enable it to be removed from the head of the screw. Second, the detent mechanism is configured to allow the user to retainably snap the drive tip into the head of the screw and, after the screw has be screwed into a destination, to remove the drive tip from the head of the screw by applying an axial force to the handle. Third, when the cannulated screw is retained on the drive tip, the screw and the driver can be slid along a guide wire disposed in the bore of the driver. Optionally, the engagement pin is spherical, and the detent mechanism is a ball detent. Also optionally the pin bias spring is a leaf spring.

In another embodiment of the present invention, there is provided a cannulated screw that includes a head and a body coupled to the head. The body has an exterior thread. Additionally: an axial bore is formed to define an interior wall of the head and of the body along a longitudinal axis of the screw; the head is shaped to receive and engage a drive tip of a driver insertable therein; and a recess is disposed in the interior wall of the head in a generally radial direction relative to the longitudinal axis to removably receive an exposable end of an engagement pin that is movable in a radially outward direction from the drive tip so as to project into the head and retain the screw on the drive tip.

In a further related embodiment, the head has an interior shape to receive and engage with the drive tip and also has a cross section that is radially asymmetrical so as to define an acceptable orientation of the drive tip in the head wherein the recess is radially aligned with the exposable end of the engagement pin. Optionally, the interior shape includes an axially disposed keyway to receive a corresponding key on the drive tip.

In another related embodiment, the head has an interior portion into which the drive tip of the driver is insertable, and the interior portion has a plurality of facets against which corresponding facets of the drive tip can be engaged. A recess is formed in each of the facets of the interior portion, so that, regardless of orientation of the drive tip in the head, the exposable end of the engagement pin will be radially aligned with one of the recesses.

In a further related embodiment, the recess is shaped to conform to the exposable end of the engagement pin. Optionally, the exposable end is tapered. As a further option, the exposable end is also rounded.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions

As used in this description and the accompanying claims, the following terms shall have the meanings indicated, unless the context otherwise requires:

A "recess" in a wall of a cannulated screw having an axial bore includes a hole forming a passageway from an exterior portion of the wall to the bore as well as an indentation in the exterior portion of the wall.

When a first component is "coupled" to a second component, the two components may be distinct components that are configured to work in cooperation with one another directly or indirectly or, alternatively, they may collectively be of unitary construction formed from a common material.

A drive tip or a corresponding shape in a screw head for receiving the drive tip is "radially asymmetrical" when each distinct exterior facet of the drive tip or each distinct interior facet of the screw head, as the case may be, in relation to the longitudinal axis thereof is not shaped identically to every other such facet. The lack of identical shape, for example, can be achieved by presence of a key on one exterior facet of the drive tip or a keyway on one interior facet of the screw head. The presence of a key or keyway on two opposing facets of six total facets, for example, in this definition is still radially asymmetrical, because not all facets are identical. The purpose of radial asymmetry in this context is to define one or more acceptable orientations of the drive tip in relation to the screw head wherein the drive tip may removably retain the screw in accordance with embodiments of the present invention.

An "acceptable orientation" of the drive tip in relation to the screw head is an orientation in which the drive tip can removably retain the screw in accordance with an embodiment of the present invention.

Figure 1:
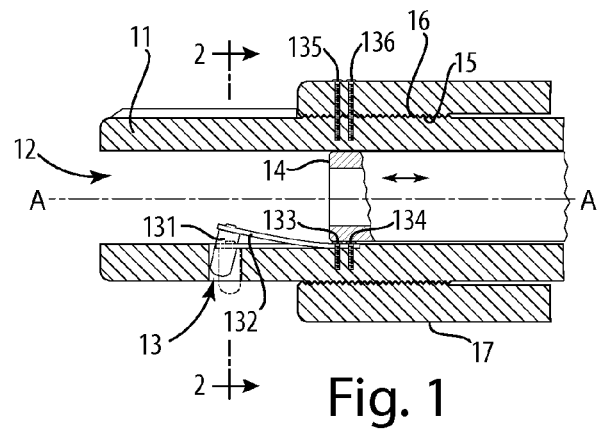
FIG. 1 is partially cut away side view of a driving end of a cannulated driver in accordance with an embodiment of the present invention.

FIG. 1 is partially cut away side view of a driving end of a cannulated driver in accordance with an embodiment of the present invention. The driver includes a hex shaped drive tip 11, which can be inserted into the head of a special cannulated screw described below in connection with FIGS. 3 through 5. An axial bore 12 is formed in the driver to define a longitudinal axis A-A.

The driver is equipped to removably retain the corresponding screw onto the driver. The drive tip 11 of FIG. 1 includes a passageway 13, disposed radially with respect to the longitudinal axis A-A, in which is movable an engagement pin 131. The pin can travel in the passageway between an extended position wherein an exposable end of the pin protrudes radially beyond the outer surface of the drive tip and a retracted position wherein the pin does not thus protrude. In the extended position, the exposable end of the pin protrudes into a corresponding recess in the head of the special cannulated screw of FIGS. 3 through 5 to removably retain the screw onto the driver.

In accordance with one embodiment of the invention herein, in order to facilitate correct insertion of the drive tip into the screw, the drive tip and a corresponding shape in the screw head for receiving the drive tip each have a cross section that is radially asymmetrical so as to define one or more acceptable orientations of the drive tip in the head. In an acceptable orientation, a recess in the screw is radially aligned with the exposable end of the engagement pin. The radial asymmetry is achieved in this embodiment of the drive tip by providing a key 111, on one of the facets of the drive tip, that projects into the interior of the drive tip.

The hex shape to the drive tip is only one of a substantial number of design choices, and the configuration of the drive tip can be modified to accommodate the choice and geometry of actuator. Specifically, in other embodiments, the radial asymmetry is achieved by making at least one of the facets of the drive tip have a dimension that is dissimilar to the dimension of another one of the sides. (By "facets" we refer to the six facets of the hex shape, presented on the exterior of the drive tip, which engage against a corresponding hex shaped arrangement of facets formed in the interior of the screw head.) In fact, the drive tip can be shaped so as to accommodate any desired actuator for moving the engagement pin, and any resulting radial asymmetry will assist in achieving the unique orientation of the drive tip in the screw head.

In a related embodiment, a recess is formed in each facet of the interior of the screw head, so that, regardless of the orientation of the drive tip in the screw head, the exposable end of the engagement pin will be radially aligned with one of the recesses, and therefore it will be possible to use the drive tip to releasably retain the screw. In this embodiment, the drive tip and the screw head will each have a cross section that is not radially asymmetrical—that is, the drive tip and the screw will each have a cross section that is in fact radially symmetrical. Consequently, in this embodiment, no matter how the drive tip is inserted into the screw head, the engagement pin 131 can be urged into an adjacent recess of the screw head.

In FIG. 1, the engagement pin is coupled to a pin bias leaf spring 132, which is mounted to an interior wall of the drive tip defined by the axial bore 12. Two screws 133 and 134 secure the pin bias leaf spring to the interior wall of the drive tip. Optionally, the pin bias leaf spring may be made of Nitinol, which has desirable shape memory properties and considerable elasticity.

At an end opposite to the end inserted into the screw head, the drive tip is rounded (as opposed to the hex shape it has for most of its length) and provided with threads 16 to screw into corresponding threads 15 in barrel 17, within which the drive tip fits concentrically. To prevent accidental rotation of the drive tip 11 relative to the barrel 17, two screws 135 and 136 are inserted through holes in the barrel 17 into threads in the underlying portion of the drive tip 11. The holes for screws 135 and 136 in the drive tip are located opposite the holes for screws 133 and 134 to facilitate drilling the latter pair of holes and placing of the latter pair of screws therein.

The pin bias leaf spring 132 biases the engagement pin to its retracted position. A hollow sheath 14 is positioned concentrically inside the barrel and the drive tip. The sheath is axially movable between a first position in which it is proximate to the engagement end of the drive tip and a second position in which it is not. It is sized so that as the sheath is advanced axially further into the drive tip into the first position, it forces the leaf spring 132 against the interior wall of the drive tip so as to move the engagement pin into its extended position. When the engagement pin 131 is in its extended position and the drive tip 11 has been inserted into a suitable screw head, the exposable end of the pin 131 protrudes radially beyond the outer surface of the drive tip, into a corresponding recess of the screw head so as to retain the screw to the driver. The exposable end is tapered and rounded to fit into a conformal recess of the screw head.

Figure 2:
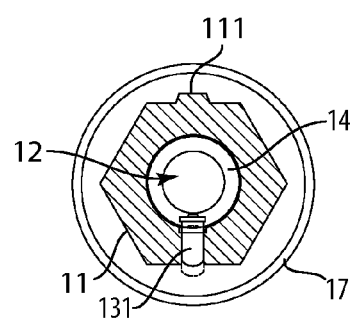
FIG. 2 is a cross section of the drive tip of the driver of FIG. 1, taken at a point just distal of the engagement pin 131.

FIG. 2 is a cross section of the drive tip 11 of the driver of FIG. 1, taken at a point just distal of the engagement pin 131, showing the drive tip 11, the engagement pin 131, the sheath 14, the axial bore 12, and, as will be described below, key 111.

Figure 3:
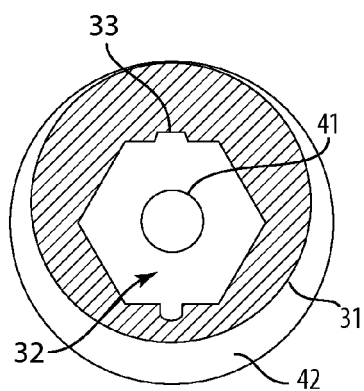
FIG. 3 is an end view of a cannulated screw for use with the driver of FIG. 1 in accordance with an embodiment of the present invention.
Figure 4:
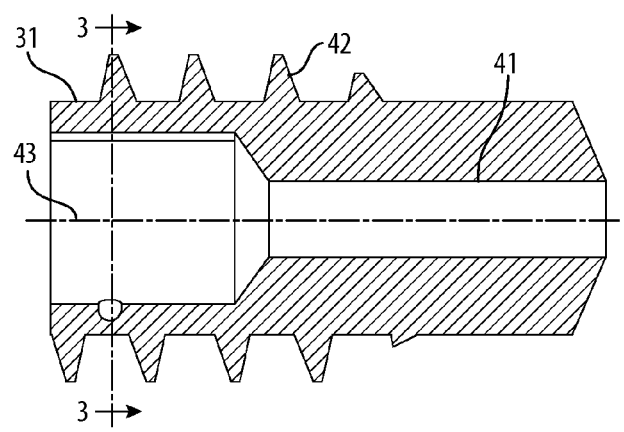
FIG. 4 is a side view of the cannulated screw of FIG. 3.
Figure 5:
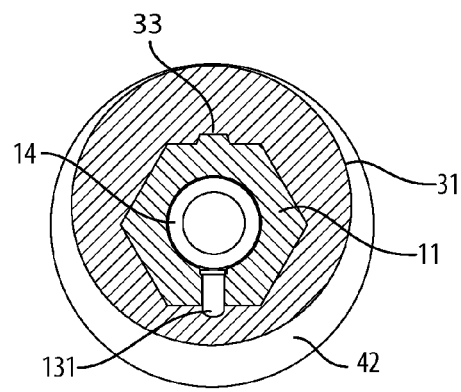
FIG. 5 is an end view of the cannulated screw of FIG. 3 showing in cross section also the drive tip after insertion into the screw.

FIG. 3 is an end view of a cannulated screw in accordance with an embodiment of the present invention for use with the driver of FIG. 1 and FIG. 4 is a side view of the cannulated screw of FIG. 3. FIG. 5 is an end view of the cannulated screw of FIG. 3 showing in cross section also the drive tip after insertion into the screw. The screw includes a head 31 and a body with threads 42. The screw has an axial bore 32 that defines a longitudinal axis 43 of the screw. The head 31 is also shaped to receive and engage with the hex-shaped drive tip 11 of the driver of FIG. 1. Corresponding to the key 111 of the drive tip of FIG. 1 is an axially disposed keyway 33 in the head 31 of the screw, so as to define an acceptable orientation of the drive tip of FIG. 1 in the head of the screw. In fact, this screw is equipped with two keyways 33, and two corresponding recesses 41 for removably receiving the engagement pin 131 of FIG. 1, so that there are two acceptable orientations of the drive tip 11 in the head of the screw, wherein the screw can be removably retained on the drive tip.

Figure 6:
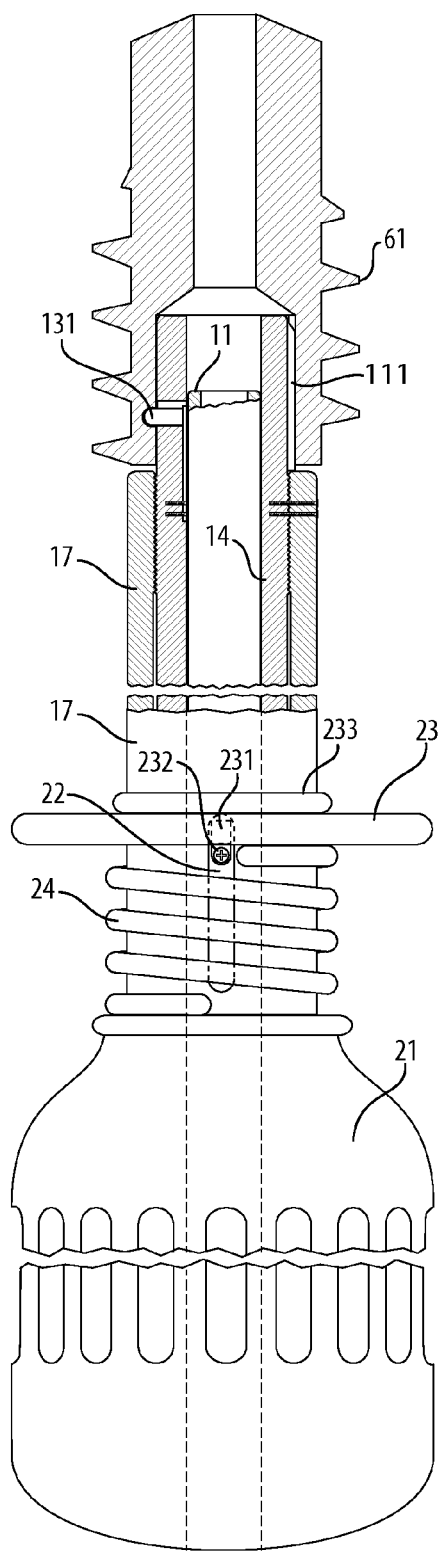
FIG. 6 is a partially cut away side view of the cannulated driver of FIG. 1, showing detail of the handle end.

FIG. 6 is a partially cut away side view of the cannulated driver of FIG. 1, showing detail of the handle end. The driver includes a handle 21 coupled to barrel 17, as well as a trigger 23 disposed axially adjacent to the handle and movable axially. The trigger 23 is coupled to tab 231, through which screw 232 attaches to the sheath 14. The tab 231 and screw 232 ride in a slot 22 formed in the barrel 17. In this way the trigger can move the sheath 14 between the first and second positions described in connection with FIG. 1. In FIG. 6, the sheath is shown in the first position, wherein the engagement pin 131 is caused by the sheath to protrude radially beyond the outer surface of the drive tip, into a corresponding recess of the head of screw 61 so as to retain the screw 61 on the driver. A sheath bias spring 24 positioned between the trigger and the end of the handle biases the sheath 14 so that it is in the first position. Stop ring 233 affixed to the barrel defines the extreme limit of axial motion of the trigger, and therefore of the sheath 14, in the distal direction. Optionally the barrel 17 includes a second slot in a position diametrically opposed to the slot 22. The trigger 24 in that event also includes a second tab diametrically opposed to tab 231, and the second tab is attached to the sheath 14 with a screw in a manner analogous to the screw 232. The sheath 14, tab 231, and screw 232 form an actuator that moves axially and causes displacement of the leaf spring 132 and the engagement pin 131 in the manner described. The user can then pull the trigger 23 toward the handle to move the sheath 14 into the second position, wherein the engagement pin 131 moves into its retracted position to release a screw head into which the drive tip has been inserted.

Figure 7:
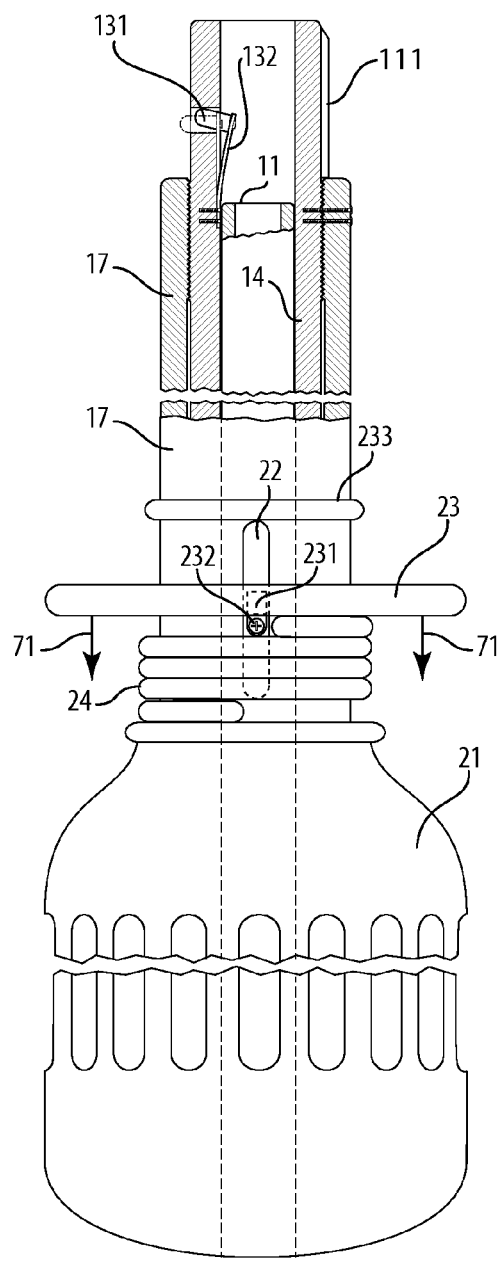
FIG. 7 is also a partially cut away side view of the cannulated driver of FIG. 1, showing detail of the handle end, but this time with the sheath shown in the second position, wherein the engagement pin is no longer forced to protrude radially beyond the outer surface of the drive tip.

FIG. 7 is also a partially cut away side view of the cannulated driver of FIG. 1, showing detail of the handle end, but this time with the sheath shown in the second position, wherein the engagement pin 131 is no longer forced to protrude radially beyond the outer surface of the drive tip, The sheath has been moved into the second position by manually urging the trigger 23 in the direction of arrows 71.

Figure 8:
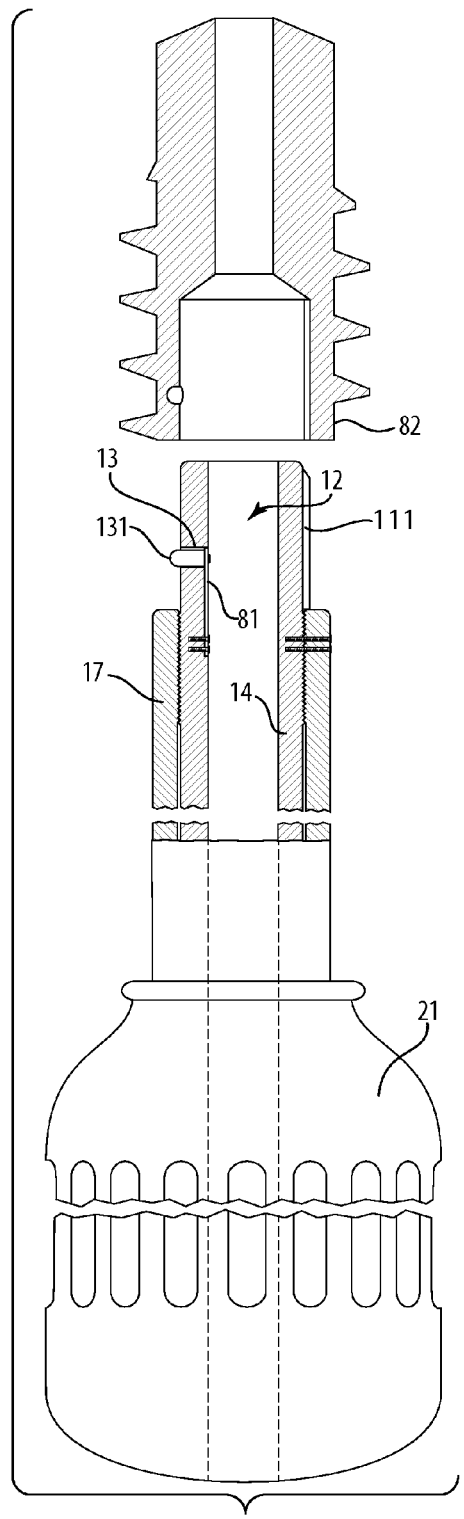
FIG. 8 is also a partially cut away side view of a cannulated driver, but in accordance with another embodiment dispensing with the actuator and trigger 23.

FIG. 8 is also a partially cut away side view of a cannulated driver, but in accordance with another embodiment dispensing with the actuator and trigger 23. In this embodiment there is provided, as before, the handle 21, the barrel 17 coupled to the handle 21, the drive tip 11 coupled to the barrel 17 and having an outer surface and an engagement end that engages within a head of a cannulated screw, and wherein the handle, barrel, and drive tip are cannulated so as to include the axial bore 12 along the longitudinal axis. The drive tip 11 similarly, as before, includes a passageway 13 disposed generally in a radial direction with respect to the longitudinal axis, and an engagement pin 131 movably mounted for travel in the passageway between an extended position wherein an exposable end of the pin protrudes radially beyond the outer surface of the drive tip and a retracted position wherein the pin does not thus protrude.

In this embodiment, the engagement pin 131 is configured in relation to the drive tip so that, in the extended position, only a rounded portion of the engagement pin 131 protrudes radially beyond the outer surface of the drive tip 11. A pin bias spring 81, which may be implemented by a leaf spring similar to leaf spring 132, biases the pin in the extended position. Note, however, that the pin bias spring 81 in this embodiment operates in a fashion opposite to the leaf spring 132: the spring urges the pin radially outwardly and operates to establish a detent mechanism in cooperation with the engagement pin in the drive tip. In this embodiment, first, in the extended position, the pin can enter a corresponding radially disposed recess formed in the head of the screw 82 to retain the screw on the drive tip and in the retracted position, the pin ceases to retain the drive tip so as to enable it to be removed from the head of the screw. Second, the detent mechanism is configured to allow the user to retainably snap the drive tip into the head of the screw and, after the screw has be screwed into a destination, to remove the drive tip from the head of the screw by applying an axial force to the handle. Third, when the cannulated screw is retained on the drive tip, the screw and the driver can be slid along a guide wire disposed in the bore of the driver. Optionally, the engagement pin is spherical, and the detent mechanism is a ball detent. Also optionally the pin bias spring 81 is a leaf spring.

Figure 9:
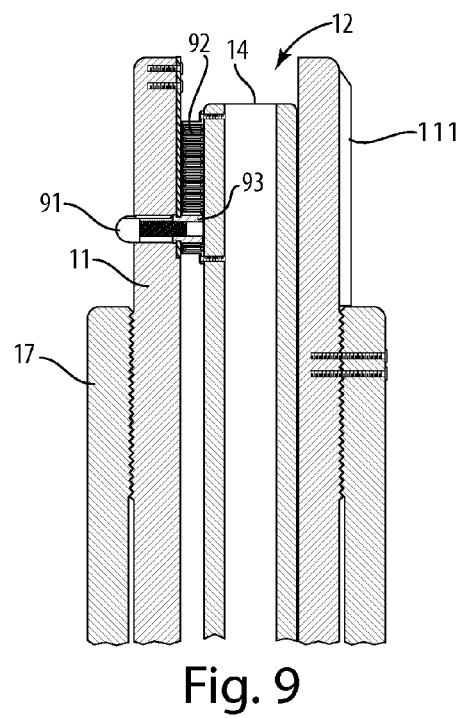
FIGS. 9 and 10 are partially cut away views of the drive tip 11 of a cannulated driver, similar that of the FIG. 1, but employing a rack and pinion in the drive tip.
Figure 10:
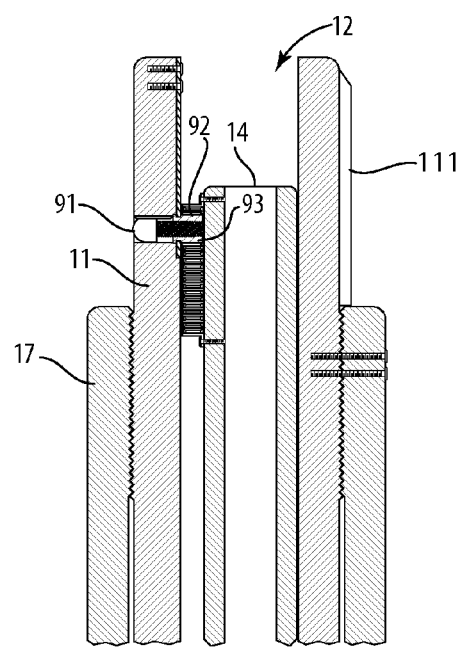

FIGS. 9 and 10 are partially cut away views of the drive tip 11 of a cannulated driver, similar that of the FIG. 1, but employing a rack 92 and pinion 93 in the drive tip. The engagement pin 91 is implemented as a screw with a keyed cross section that rides inside of pinion 93. The keyed cross section of the engagement pin 91 prevents its rotation inside the housing of drive tip 11. As a result, when the rack 92 is moved longitudinally within the drive tip 11, the rack 92 causes the pinion 93 to rotate, which in turn causes the engagement pin to move radially relative to the drive tip between the extended and retracted positions shown respectively in FIGS. 9 and 10. The rack 92 is coupled to the sheath 14, so that the rack 92 can be moved by moving the trigger 24, as in the case of FIG. 1. A benefit of this rack-and-pinion arrangement, at the expense of some greater complexity, is that the engagement pin 91 can be driven by positive action into both the retracted and the extended positions, whereas, in the embodiment of FIG. 1, the motion of the pin in one direction is dependent on action of the leaf spring 132.

Although we have described the drive tip and the screw head has having a hex-shaped cross section, the choice of six sides is somewhat arbitrary. Four or five may be used, for example. Alternatively the cross-sectional shape of the drive tip insertable into the screw head may be generally round and include a series of keys that are radially asymmetrically located so as to define one or more acceptable orientations of the drive tip in the screw head, and the screw head interior may be correspondingly shaped to receive and engage with the drive tip.

The driver may be constructed of stainless steel, Nitinol, or other materials suitable for use in a surgical environment.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A cannulated screw comprising:
a head;
a body coupled to the head, the body and the head having an exterior thread, the exterior thread extending along a length of the head;
wherein:
the head and the body have a combined length corresponding to a length of the screw;
an axial bore is formed to define an interior wall of the head and of the body along a longitudinal axis of the screw, the axial bore extending the entire length of the screw;
a majority of the body along its length has a substantially cylindrical profile;
the head is shaped to receive and engage a drive tip of a driver insertable therein, the head having a core diameter that transitions smoothly and continuously from a core diameter of the body; and
a recess projects, from the axial bore, along a radial projection axis into the interior wall of the head, the recess having an inner surface, formed in the interior wall, the surface completely surrounding the projection axis upon entry into the recess, the recess shaped to removably receive an exposable end of an engagement pin that is movable in a radially outward direction from the drive tip so as to project into the head and retain the screw on the drive tip.

2. A cannulated screw according to claim 1, wherein the recess is a passageway from the interior wall of the head to an exterior portion of the head.

3. A cannulated screw according to claim 1, wherein the recess is an indentation.

4. A cannulated screw according to claim 1, wherein the head has an interior shape to receive and engage with the drive tip and also has a cross section that is radially asymmetrical so as to define an acceptable orientation of the drive tip in the head wherein the recess is radially aligned with the exposable end of the engagement pin.

5. A cannulated screw according to claim 4, wherein the interior shape includes an axially disposed keyway to receive a corresponding key on the drive tip.

6. A cannulated screw according to claim 1, wherein the recess is shaped to conform to the exposable end of the engagement pin.

7. A cannulated screw according to claim 1, wherein the head has an interior portion into which the drive tip of the driver is insertable, the interior portion having a plurality of facets against which corresponding facets of the drive tip can be engaged, and a recess is formed in each of the facets of the interior portion, so that, regardless of orientation of the drive tip in the head, the exposable end of the engagement pin will be radially aligned with one of the recesses.

8. A cannulated screw according to claim 1, wherein the exposable end is tapered.

9. A cannulated screw according to claim 8, wherein the exposable end is also rounded.

* * * * *